United States Patent [19]

Wojdani

[11] Patent Number: 5,275,814
[45] Date of Patent: Jan. 4, 1994

[54] ALLERGEN-THYMIC HORMONE CONJUGATES FOR TREATMENT OF IGE MEDIATED ALLERGIES

[75] Inventor: Aristo Wojdani, Los Angeles, Calif.

[73] Assignee: Allergy Immuno Technologies, Inc., Newport Beach, Calif.

[21] Appl. No.: 728,185

[22] Filed: Jul. 10, 1991

Related U.S. Application Data

[62] Division of Ser. No. 534,237, Jun. 7, 1990, Pat. No. 5,116,612, which is a division of Ser. No. 65,310, Jun. 23, 1987, Pat. No. 4,946,945.

[51] Int. Cl.$^5$ .................. A61K 39/35; A61K 39/36; A61K 39/38; A61K 37/24
[52] U.S. Cl. .................. 424/91; 424/88; 424/89; 424/92; 424/93 A; 424/93 D; 530/301; 530/365; 530/370; 530/379; 530/395; 530/397; 530/399; 530/402; 530/403; 530/404; 530/405; 530/406; 530/408; 530/409; 530/410; 435/174; 435/177
[58] Field of Search .............. 530/402, 403, 404, 405, 530/406, 408, 409, 410, 395, 397, 301, 399, 365, 370, 379; 424/88, 91, 92, 89, 93; 435/174, 177; 574/2, 12, 8, 21, 54

[56] References Cited

U.S. PATENT DOCUMENTS

| | | | |
|---|---|---|---|
| 4,003,792 | 1/1977 | Mill et al. | 424/91 |
| 4,055,633 | 10/1977 | Goldstein | 436/539 |
| 4,124,700 | 11/1978 | Goldstein | 436/545 |
| 4,140,679 | 2/1979 | Malley | 424/88 |
| 4,261,973 | 4/1981 | Lee et al. | 424/91 |
| 4,432,969 | 2/1984 | Batchelor | 424/91 |
| 4,609,547 | 9/1986 | Garman et al. | 424/88 |
| 4,946,945 | 8/1990 | Wojdani | 530/402 |
| 5,075,109 | 12/1991 | Tice et al. | 424/88 |
| 5,080,896 | 1/1992 | Visser et al. | 424/88 |
| 5,116,612 | 5/1992 | Wojdani | 424/85.2 |

OTHER PUBLICATIONS

Goldstein et al (1972) "Purification and Biological Activity of Thymiosin a Hormone of the Thymus Gland" Proc. Natl. Acad. Sci USA 69(7):1800–1803.

Sztein et al (1986) "Modulation of Interleukin 2 Receptor Expression on Normal Human Lymphocytes by Thymic Hormones" Proc. Natl. Acad. Sci USA 83:6107–6111.

Serrate et al (1987) "Modulation of Human Natural Killer Cell Cytotoxicity Activity, . . . by Thymic Hormones" J. Immunology 139:2238–2343.

Primary Examiner—Kay K. Kim
Attorney, Agent, or Firm—James A. Quinton; Frank Frisenda, Jr.

[57] ABSTRACT

A protein conjugate or mixture useful in immunotherapy composed of a biological response modifier (BRM) and an allergen is disclosed. In use the protein conjugate or mixture is combined with a pharmaceutically acceptable carrier. Cytokines, bacterial, fungal and viral immunopotentiators and thymus hormones are disclosed as suitable BRM's for use in the invention.

10 Claims, 2 Drawing Sheets

ALLERGEN-THYMIC HORMONE CONJUGATES FOR TREATMENT OF IGE MEDIATED ALLERGIES

This application is a divisional of co-pending Ser. No. 534,237 filed Jun. 7, 1990 now U.S. Pat. No. 5,116,612 which is a division of application Ser. No. 065,310, filed Jun. 23, 1987 now U.S. Pat. No. 4,946,945.

BACKGROUND OF THE INVENTION

1. Field of the Invention

The present invention relates to the treatment of allergies. Allergic disorders affect as many as one in four Americans (59,000,000). More than 17% have upper respiratory allergies, including hay fever. Another 4% have asthma, and 10% have allergic skin conditions such as eczema and other rashes. It is estimated that some 40,000,000 school days are lost yearly because of asthma, in addition, approximately 6,000 lives are lost to asthma, and dozens die of insect bites, annually. The accepted allergy treatment method is hyposensitization injections containing minute amounts of allergens causing the reaction, given in incremental doses once or twice weekly until symptoms improve, and then maintained at a set dosage with decreasing frequency for approximately three years. If carefully selected, approximately one-third of patients find their symptoms are relieved substantially by this therapy. The rest have mild to moderate improvement. This immunotherapy method has been standard practice since 1911. The present invention provides a method of immunotherapy and a modified allergen extract and a method of making the modified allergen extract.

2. Description of the Prior Art

Modified allergen extracts for use in immunotherapy have been reported in the literature. Such extracts have been modified with the desire to reduce their allergenicity without sacrificing immunogenicity and hence achieve improved immunotherapy results with fewer injections. Polymerized grass pollen allergens have been prepared and tested in immunotherapy. See, Patterson et al., "Polymerization of Individual Species of Grass Pollen Allergen", *J. Allergy Clin. Immunol* 72:129-133, (1983); Fitzsimons et al., "A comparison of the Immune Response to Immunotherapy with Polymerized Grass Allergen and Monomeric Grass Allergen"; *Annals of Allergy* 57:291-294 (1986); Fitzsimons et al., *supra* reports that polymerized and monomeric grass pollen extract give comparable result in immunotherapy. Further reports have suggested that the polymerized grasses contain an increased amount of immunity producing allergen. It has been reported that in use a series of fifteen (15) injections with the polymerized pollen are as effective as a series of seventy (70) standard injections. Modified allergens for allergy desensitization have also been prepared by treating pollen extract with formaldehyde. Such formaldehyde treated allergens are referred to as "allergoids". Polyethylene glycol modified ragweed extracts have also been proposed for use in immunotherapy. See Juniper, et al. "Polyethelene Glycol—Modified Ragweed Extract: Comparison of Two Treatment Regiments". *J. Allergy Clin Immunol* 78: 851-6 (1986). See also U.S. Pat. No. 4,180,562 (Patterson) which discloses the use of ragweed polymerized extracts in immunotherapy.

Other chemically modified allergens have been suggested in the art.

The following summarizes the types of chemically modified allergens and their modes of action.

TABLE 1

| CHEMICALLY MODIFIED ALLERGENS | | |
|---|---|---|
| Name | Treatment | Effect |
| Allergoid | Formalin | Allergenicity ↓ Antigenicity → |
| PER | Pyridine Exposed | Allergenicity ↓ Antigenicity → |
| Pollinex | Glutaraldyhyde-Modified, Tyrosine-Adsorbed | Allergenicity ↓ Antigenicity → |
| PRW | Polymerized Ragweed Allergens | Allergenicity ↓ Antigenicity → |
| PEG | Monomeric Coupling of Polyethylene Glycol to Allergen | Enhancement of T-Suppressor Cells |
| DG-L | Conjugation of D-Glutamic Acid: D-Lysine To Allergen | B-Cell Tolerance |

↓ = decreased.
→ = remained unchanged.
↑ = increased.

From: Perelmutter, L. Lymphocyte Response in Allergic Patients During Immunotherapy in: Allergy-Immunologic and Management Considerations PP. 13-26 Edited by J. T. Spencer, Published by Meded Inc., 1982 Miami, Fla.

See: Marsh, D. G., Lichtenstein, L. M., Campbell, D. H.: "Conversion of Group I Rye Pollen Allergen to 'Allergoid' by Mild Formation Treatment" *Immunology* 18:705, 1970.

Furic R., Peremutter L., Goodfriend L.: "Modification des Properietes Allergeniques et Antigeniques d'un Extrait d'Ambroisic." Presented at the Fourth International Congress of Immunology, Paris, July 1980.

Patterson, R., Suszko, J. M., Pruzansky, J. J., et al: "Polymerization of Mixtures of Grass Allergens." *J. Allergy Clin Immunol* 59:312f, 1977.

Lee, W. Y., Sehon, A. H.: "Suppression Reaginic Antibodies." Immunol Rev 41:200, 1978.

Katz, D. H., Homoaka, T., Benneceraaf, B.: "Introduction of Immunological Tolerance in Bone Marrow Derived Lymphocytes of IgE Antibody Class." Proc Natl Acad Sci USA 70:2776, 1973.

SUMMARY OF THE INVENTION

The presence of IgE in patient serum was recognized as an indication of allergic disease in 1967 by Johansson and Bennich. Control of IgE mediated disease is believed to require a suppression of IgE production in the body. According to the present invention, modified allergy immunotherapy agents are supplied which in use result in a suppression of the production of IgE in response to the allergen and a stimulation of the production of IgG against the allergen.

The present invention provides highly effective immunotherapy agents for treatment of IgE mediated allergies, a method of making the allergy immunotherapy agents and a highly effective immunotherapy regimen. Examples of substances that are known allergens abound. For example milk, house dust, ragweed, grass pollen, tree pollen, fish, dog dander, cat dander, horse dander, bee venom, wasp venom, chocolate and eggs are common allergens. According to the invention, a combination of allergen and biological response modifier is provided for use in allergy immunotherapy.

The term, biological response modifier (hereinafter also referred to as BRM) includes a large number of agents; immunomodulating and immunorestorative agents; thymic factors; antitumor and antilymphoid cell antibodies; tumor antigens and modifiers of tumor antigens on cell membranes, antigrowth factors; and maturation and differentiation factors. Biological response modifier can be prepared from the following sources:

1. Chemical synthesis.
2. Cellular antigens or products.
3. Animal tissue or cell extracts.
4. bacterial antigens.
5. Fungal antigens.
6. Viral antigens.
7. Plants antigens or extracts.
8. Invertebrate cells or tissue product.

The biological response modifier (BRM) are optionally but preferably linked to the allergen by covalent bonds. The biological response modifiers are preferably selected from cytokines most preferably lymphokines, or monokines, thymic factors and bacterial, viral and fungal agents which are inducers of lymphokines. In use, the immune response is enhanced in such a way that results in the production of IgG against both the BRM and the allergen. Thus the production of IgE is eliminated or substantially reduced as a result of immunotherapy according to the invention.

The use of the immunotherapy agents of the invention will result in more effective immunotherapy and allow a substantial reduction in the number of injections to achieve a comparable degree of immunotherapy compared to immunotherapy performed with conventional allergen extracts.

DETAILED DESCRIPTION OF THE INVENTION

In accordance with the present invention, it has been found that a highly effective immunotherapy agent is provided by a combination of an allergen to which the patient is allergic and a biological response modifier. Improved immunotherapy results can be obtained by using the combination of allergen and BRM.

According to the invention, the biological response modifier is preferably linked to the allergen in question by covalent bonding. Preferably the BRM according to the subject invention is selected from the group of cytokines, bacterial immunopotentiators, viral immunopotentiator, fungal immunopotentiators, and thymic factors.

The bacterial immunopotentiators are preferably mycobacteria, most preferably attenuated bovine-type Bacillus Calmette Guerin (BCG) and mutations thereof.

Particularly useful as BRM's according to the invention are products derived from the mycobacteria, for example the MER (methanol extraction residue) performed according to the methods described in Weiss, D. W. (1976) "MER and Other Mycobacterial Fractions in the Immunotherapy of Cancer"; Symposium on Immunotherapy in Malignant Disease, pp. 473-497 Vol. 60 (Medical Clinic of North America); Ben-Efraim, S., "Methanol Extraction Residue Effects and Mechanism of Action": *"The Modulation of Immunity"*, edited by M. S. Mitchell, Pergamon Press, Los Angeles, USA, pp. 303-337, 1985 which are hereby incorporated by reference. Such methanol extraction products of BCG have been found to be particularly useful in the subject invention.

BCG can be obtained from various depositories, for example, BCG strain number ATCC 35.734 or TMC 1101 (Trudeau Mycobacterial Culture Collection, Trudeau Institute, Saranac Lake, N.Y.). Different fractions of this bacteria (for example: cell walls from BCG, cell wall skeleton from BCG, muramyl dipeptides (N-Acetylmuramyl-L-Ala-D-Glu-NH2), methanol extract residues (MER), and PPD (purified protein derivative) are known in the art. Many are commercially available from, for example, RIBI Immunochem Research Inc., Hamilton, Mont. 59840, USA. See, M. S. Mitchell and R. I. Murahata, "Modulation of Immunity by Bacillus Calmette-Guerin (BCG)," Chap. 7: in *The Modulation of Immunity*, edited by M. S. Mitchell Pergamon Press, Los Angeles PP. 275-301 (1985) which is incorporated herein by reference.

Such fractions are preferably used in this invention. The use of non-toxic fractions of BCG as the BRM according to the invention result in an effective immunotherapy agent which lack the toxicity sometimes associated with BCG.

Particularly useful in the subject invention are the following fractions derived from BCG cultures, purified protein derivative (PPD), methanol extract residue (MER), muramyl dipeptides (MDP), cell walls, cell wall skeletons and the chloroform soluble peptidoglycolipid active fractions of BCG cultures referred to as Wax D. Other fractions of BCG cultures that are also useful as BRMs include the water soluble and lipid free fraction having adjuvant activity prepared according to Hui, *Nature, New Biol.* 238:241-42 "Water Soluble and Lipid Free Fraction From BCG" (1972) which is hereby incorporated by reference.

Purified mycobacterial cell wall components particularly BCG cell wall components showing immunostimulating activity are useful BRMs according to the invention. Peptido-glycolipid cell wall skeleton CWS-I; toxic free lipid 'P 3' cord factor; and a sulpholipid fraction; cell wall fractions containing at least N-acetylmuramyldipeptide of mycrobacteria particularly of BCG are useful BRMs. Immunostimulating or adjuvant activity is determined by testing in guinea pigs using hen egg-white lysozyme as antigen and incorporating the fraction in oil-detergent mixture (Freund's incomplete adjuvant). See: Azuma, et al. (1974) "Biologically Active Component From Mycobacterial Cell Walls. I. Isolation and Composition of Cell Wall Skeleton Component P3." *J. Natn. Cancer Inst.* 52; 95-107; Meyer, et al. (1974) *J. Natn. Cancer Inst.* 52; 103-11 Goren, M. B. (1974) *In: International Symposium on Immunostimulants, Proceedings Paris* which are hereby incorporated by reference.

Another example of a mycobacteria useful in the subject invention is M. tuberculosis strain Aogama B and mutations thereof for example as described in Kumazawa, Y. Shibusawa, A., Suzuki, T. and Mizunoe, K. (1976) "Separation of an Adjuvant-Active Glycolipid Lacking Peptide Moiety from Wax D Preparation of Mycobacterium Tuberculosis Strain Aoyama B." *Immunochemistry* 13:173-177 which is incorporated by reference. For example, the active glycolipid lacking peptide separated from wax D of Aogama B is a useful BRM.

Other examples of microorganisms useful in the invention as a source of BRMs include *candida albicans* and mutations thereof, e.g. ATCC 18804; CBS 562, MacKinnon 572 (IFO 1385) for example, C. Tropicalis available from the ATCC, and mutations thereof, 2-corynebacterium parvum and mutations thereof. *Candida albicans* (heat inactivated, and fractions of this microorganism are prominant immunomodulator as manifested by highly increased activity of natural killer cells in mice pretreated with this microrganism. See: Vismara, D., Lombardi, G., Piccolella, E. and Colizzi, V. *Infect. Immun.*, 49, 298 (1985); Marconi, P., Scaring, L., Tissi, L., Boccanera M., Bistoni, F., Bonmassar, E. and Cassoni, A. *Inf. Immuno.*, 50, 297, (1985); and Segal E., Nussbaum, S., Barnea, Y. *Sabouraudia*, 23, 275, (1985).

Particularly useful are cell culture products of *C. Parvum* and residue extracts such as methanol and pyridine residue extracts. For example, *C. Parvum* (WC) whole cell, *C. Parvum* (PE) Pyrine Extract and *C. Parvum* (PER) pyridine extract residue are useful BRM's according to the invention. Such products are available commercially from, for example: RIBI, Immunochemicals, Hamilton, Mt.

*Eschrichia Coli, Salmonella Typhi,* Pneumococcus, Streptococcus, Staphylococcus and other gram positive and gram negative bacteria and cell culture products derived therefrom are also useful as BRM's according to the invention.

Thymic hormones have also been found to be useful as the BRM for mixture with and/or coupling to the allergen for immunotherapy treatment. Thymic hormone thymopoietin of mammalian origin preferably bovine or mouse and most preferably sheep is a useful BRM for mixing or coupling with the allergens according to the subject invention. Preferentially the TF5 fraction of thymus hormone is used as the BRM of thymus origin according to the invention.

Thymic hormones are complex and likely to contain more than one active factor. Thus, thymic hormone secretions have been divided into fractions. Thymosin fraction 5 (TF5) is a bovine preparation of thymus containing 40-50 component peptides, of which several $\bar{a}_{11}$, $\beta_1$, $\beta_3$, $\beta_4$, $\beta_7$, $\beta_8$, $\beta_9$, $\beta_{10}$, and $\beta_{11}$) have been isolated and sequenced as described in Goldstein, et al. "Current Status of Thymosin and Other Hormones of the Thymus Gland", *Recent Prog Horm Res* 1981:37:369-415 which is hereby incorporated by reference. TF5, and two of its component peptides that have been synthesized, thymosin $\bar{a}_1$ (T$\bar{a}_1$) and thymosin $\beta_4$ (T$\beta_4$), have been reported to be biologically active in promoting T cell differentiation and/or modulating T cell function. See, Wang, et al. "Solid Phase Synthesis of Thymosin $\bar{a}_1$.", *Int J Pept Protein Res* 1980; 15:1-5. In addition to TF5, T$\bar{a}_1$, and T$\beta_4$ several other thymic tissue extracts, peptides, and serum factors have been reported to be members of a family of thymic hormones that influence T cell differentiation and function.

TF5 is believed to have the important biological property of enhancing phytohemagglutinin (PHA)-induced interleukin-2 (IL-2) production by human peripheral blood mononuclear leukocytes (PBL) and IL-2 and colony stimulating factor production by murine, PNA-thymocytes, and lymph node lymphocytes (i.e., mature T cells). Published results indicate that this in vitro biological activity of TF5 does not reside with either of its well-characterized component peptides, T$\bar{a}_1$ or T$\beta_4$. See Zatz, et al. "Comparison of the Effects of Thimosin and Other Thymic Factors on Modulation of Interleukin-2 Production", *J.B. Response modifiers* 4:365, (1985).

The biologically active factors of thymic hormones can be isolated from calf thymuses by homogenization, ultracentrifugation and dialysis. The active dialyzate is further purified by gel filtration of Sephadex G-10 and G-25 columns, and later by anion exchange chromatography. Each fraction is measured for activation of T cell function, induction of interleukin-2 and interferon production in vitro, Thymopoietin TF5 is also available commercially from, for example, Serva Fine Biochemicals, Garden City Park, Long Island, N.Y.

Lentinan is another BRM which is useful in the subject invention. Lentinan is an immunopotentiating polysaccharide and is a fully purified B-1, 3 glucan with B-1,6 branches obtained from *lentinus edodes*. Lentinan can be produced according to the methods described in Chihara, G., et al. "Fractionation and Purification of the Polysaccharides with Marked Antitumor Activity; Especially Lentinan from Lentinus Edodes (Berk). Sing. (An Edible Mushroom)" *Cancer Research*, 30:2776-2881, 1970.

In addition, cytokines preferably lymphokines and monokines are useful for mixing with or coupling to the allergens according to the subject invention. Cytokines are the soluble products released by immunologically active cells other than antibody and transfer faction. Monokines (MK) are the macrophage products. Different biological activities have been ascribed to lymphokines produced by activated leukocytes. Two different lymphokines are believed responsible for many central aspects of immunity. The factor produced by activated mononuclear phagocytes, which is essential for supporting both T and B cell responses was named Interleukin 1 (IL1), whilst the factor produced by activated T cells which supports T cell proliferation in vitro was named Interleukin 2 (IL2). Subsequently a T cell product that induces colony formation of stem cells was named Interleukin 3 (IL3).

The importance of these interleukins to the development and maintenance of immune responses has led to much effort being devoted to their production and assay. See, Cohen, S. E. Pick and J. J. Oppenheim (eds), 1979, *Biology of the Lymphokine* (Academic Press, New York); Aarden, L. A., et al. 1979, *J. Immunol.* 123, 2928; Ihle, J. N., L. Pepersack, and L. Rabar, 1981, *J. Immunol.*, 126, 2184; which are hereby incorporated by reference.

Interleukin-1, Interleukin-2, Interleukin-3, Interferon; Lymphotoxin and, natural killer cytotoxic factors. Interleukin-1, Interleukin-2, Interleukin-3, Interleukin-4, Interferon, particularly $\gamma$ interferon, Lymphotoxin and natural killer cytotoxic factors are also usefully coupled to and/or mixed with the allergens according to the subject invention. Such BRMs are commercially available and described in the prior art. See, Epstein, L. B., "The Comparative Biology of Immune and Classical Interferons" in: Cohen, S., Pick, E., and J. J. Oppenheim (EDS) 1979, "Biology of the Lymphokines" (Academic Press New York); Klostergaard, J., Goodsel, D. and G. A. Granger: "Induction and Characterization of Lymphotoxins From Tumor Promoter Synerized, Lectin-Stimulated Human Lymphocyte In Vitro" *J. of Biological Response Modifiers* 4:195, (1985); Blanca, I, Herberman, R. B., and J. R. Ortaldo, "Human Natural Killer Cytotoxic Factor", *Nat. Immun. Cell Growth Regul.* 4:48, (1985).

According to the subject invention the allergens are mixed with the BRM's and injected into the patient undergoing immunotherapy. Preferably the BRM's are covalently bound to the allergens and then periodically injected into the patient undergoing immunotherapy in a therapeutically effective amount and mixed with a pharmaceutically acceptable diluent, such as 0.85% sodium chloride or different buffers. In another aspect of the invention the production of allergen specific IgG can be enhanced in mammals by the injection of a therapeutically effective amount of BRM and allergen.

Preferably when the BRM and allergen are coupled, the coupling is done according to the following method.

For example, the allergen is attached to bacterial antigens and biological products such as thymopoietin and interleukin-1, or interleukin-2 by reacting with a EDAC (1-ethyl-3 dimethylaminopropyl) carbodimide-hydrochloride coupling agent. The reaction mechanism involves two steps: the activation of the carboxyl groups, and the displacement of the nucleophile. e.g., R-NH2, releasing the EDAC as a soluble urea derivative. The activated carboxyl will be coupled to the amino group in the reaction mixture. In performing such process the bacterial proteins (2 mg/ml) and Interleukin-1 (1,000 unit/ml) and thymopoietin (100 ug/ml), Interleukin-2 (1,000 units/ml) are dissolved in carbonate buffer pH 9.6 and allergens at a concentration of about 2 mg/ml are dissolved in an acetate buffer. The pH is corrected to between 4.7 and 5. One ml of protein is then added to 1 ml of allergen. The pH is then adjusted between 4.7 and 5 using HCl and 4 mg of EDAC. The reaction proceeds for 2 hours. The resulting mixture is dialysed and different fractions are separated using gel chromatography. The allergen bound to the bacterial agent is thus separated.

A different approach to the chemical crosslinking technique is preferably used for binding of polysaccharides to allergens and involves production of free aldehyde functional groups on the polysaccharides. This is achieved by periodate oxidation of bacterial polysaccharides whose carbohydrate component is converted to free aldehyde groups. Then this aldehyde group binds with the aminogroup of allergen which by addition of sodiumborohydride treatment reduces to a stable secondary amino bond creating a covalent cross-linkage between the immunomodulator and the allergen.

Other cross-linking chemicals such as N-hydroxysuccinimidyl 3-(2-pyridythio) propionate (SPDP), Toluidine Diisocyanate (TDIC), and others can be used in these reactions.

Alternatively allergens can be bound to thymopoietin and interleukin-1, interleukin-2 and interleukin-3 as follows:

BRM-allergen conjugates are prepared primarily with heterobifunctional cross-linking reagents. These cross-linkers have an amino reactive NHS-ester as one functional group and a sulfhydryl reactive group as the other. First e-amino groups of surface lysine residues are acylated on proteins that lack free sulfhydryl groups with the NHS-ester.

Next, a second protein is introduced that possesses free sulfhydryl groups to be modified by way of a thiol reactive group. Common thiol reactive groups are maleimides, pyridyl disulfides, and active halogens.

Another coupling procedure that can be used involves the use of MBS. The mechanism of the reaction is as follows:

Thus, M-Maleimidobenzoyl-N-Hydroxysucciminide ester (MBS) preferably can be used for the binding of thymopoietin and interleukin-1, 2, and 3 with different allergens. This method has been described in the art for binding one protein to another See for example, Youle, R. J. and Neville, D. M. Jr. (1980) Proc. Natl. Acad. Sci. USA 77, 5483-5486; Kitagawa, T., Kawasaki, T. and Munechika, H. (1982) J. Biochem 92:585-590; Freytag, W. J., Dickinson, J. C. and Tseng, S. Y. (1984) Clin Chem. 30, 417-420 which are herein incorporated by reference.

While applicant does not wish to be bound by any theory of operation of the subject in invention, it is believed the subject invention is useful in treating allergy by controlling synthesis of IgE. A cellular model system that explains B cell differentiation during IgE synthesis and T cell control has been proposed. Control of IgE mediated allergic disease appears to require control of IgE synthesis initiated by precursor B cells. The continued treating of the end product, the sensitized target organs responsible for mediator release, appears as the only, less desirable alternative, allowing continuing precursor IgE B cell production in the host. This modality of controlling IgE-mediated disease requires long term immunotherapy.

By binding allergens to BRMs, it is believed that BRMs activates the T helper cells in such a way that they interact with Pre B cell (Precusor B cell) which carry Fc receptor of IgG on their surface but not the Pre B cells carrying IgE receptors. Therefore, the memory cells for the allergens will be plasma cells producing or secreting IgG but not IgE.

The following examples will serve to illustrate further the present invention:

EXAMPLE 1

Biological Response Modifiers a) Candida-albicans extract (CA) was obtained from ATCC, catalog 18804. An extract was prepared as follows:

Fractionation of CA

Figure 1:
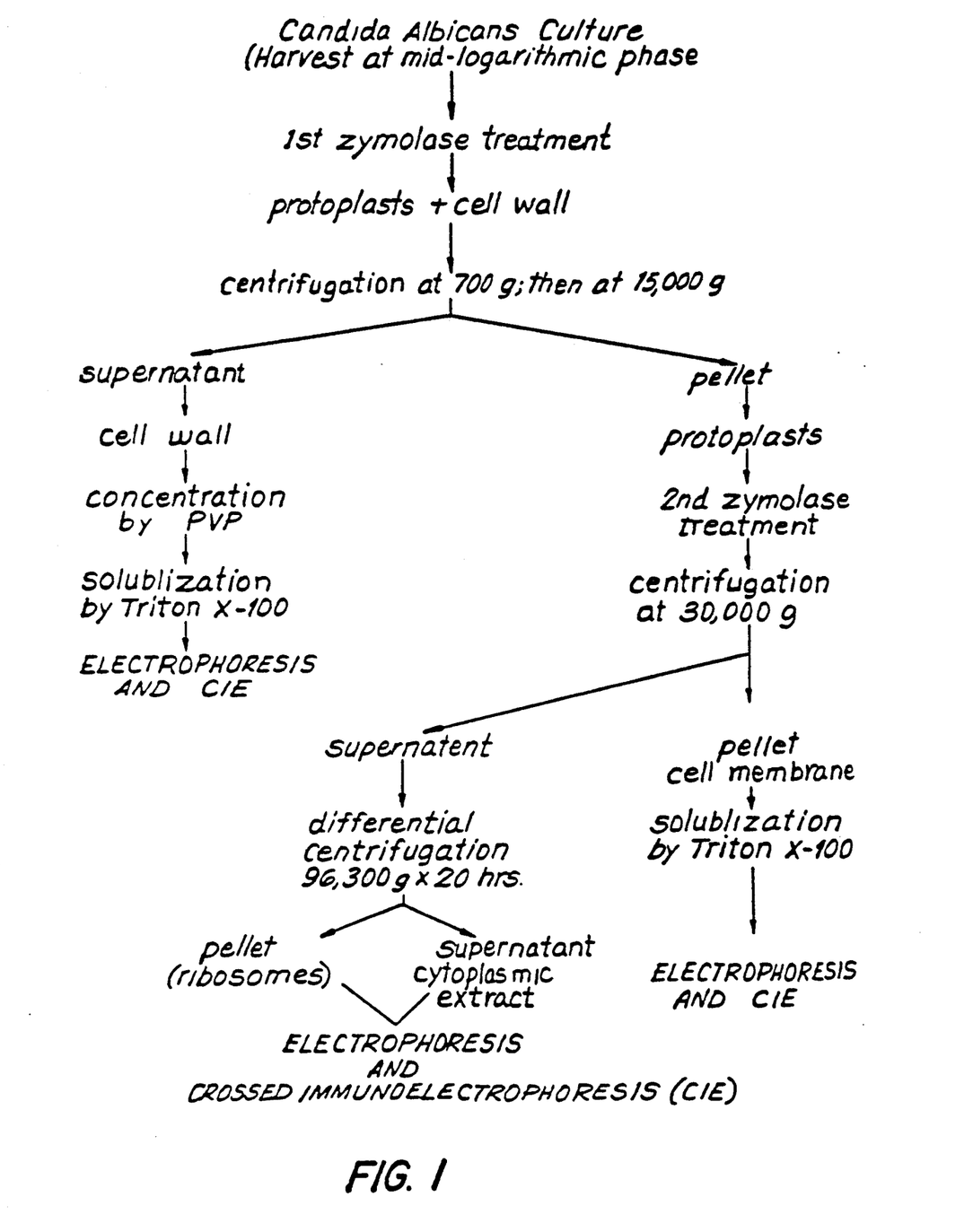
FIG. 1 is a schematic presentation of preparation of candida fractions for use as a BRM according to invention.

The yeast was grown in Sabouraud medium containing polypeptone yeast extract and glucose according to the method of Hopwood, V., Evans, E. G. V. and Carney, J.A., J. Immunol. Methods, 80, 199, (1985). The culture was incubated at 28° C. with slight agitation until mid-logarithmic phase, harvested by centrifugation and washed three times with 0.1M phosphate buffered saline. For the preparation of candida fractions, two different methods were used. The first, the method of Segal et al (1985) Sabouraudia, 23,275, for preparation of cytoplasmic cell extracts and ribosomes and the second according to Kobayashi and Suginaka Sabouraudia, 22, 341 for the preparation and comparison of cell wall and cell membrane proteins from different candida species. A combination of these two procedures provide the format for this present study as shown in FIG. 1.

The yeast was harvested by centrifugation at 10,000 g at 4° C., washed three times with cold tris buffer (tris [hydroxymethyl] aminomethane-hydrochloride 0.01M buffer, supplemented with 0.1M NaCl and 0.03M $MgCl_2$, pH 7.4) (TMB) and resuspended in three volumes of TMB.

To prepare the cell wall protein, protoplasts were obtained by shaking the cells for 30 minutes at 37° C. in buffer containing zymolyase 60,000 (500 ug/ml), phenylmethylsulfonyl fluoride (60 ug/ml) and 2M sorbitol. The supernatant was centrifuged at 700 g for three minutes then at 15,000 g for 15 minutes. The sedimented protoplasts was observed under the light microscope. The supernatant, which retained the cell wall protein was concentrated by the use of polyvinylpyrolidone. The protoplast was then used for the preparation of cell membrane, ribosomes and cytoplasmic cell extract. To prepare the membrane proteins, protoplasts were lysed completely with zymolase as above, but without sorbitol. After centrifugation at 30,000 g, the precipitate containing the membrane fragment was washed three times in the same buffer and maintained at -70° C. until used. The supernatant was used for the preparation of ribosomes and the cytoplasmic extract. For this purpose, the supernatant of 30,000 g centrifugation was layered on sucrose-ammonium sulfate solution (15 and 5% w/v, respectively) in tris buffer and centrifuged at 96,000 g at 4° C. for 20 hours. Supernatant, after this centrifugation were designated cytoplasmic cell extract and pellet the ribosomes.

Preparation of polysaccharide fraction. A polysaccharide fraction was extracted from C. albicans according to the procedure described by Vogel, R. A., "The Polysaccharides of Candida Albicans", Proc. Soc. Exp. Biol. Med. 86:373, 1954. This polysaccharide (labeled Mangion purified polysaccharide, MPPS) was obtained by autoclaving C. albicans yeast cells, precipitating the supernatant fraction with 95% ethanol, and deproteinizing the preparation 10 times with a mixture of butanolchloroform. MPPS was characterized as a polysaccharide containing glucose and mannose by qualitative ascending chromatography, and 3.1% protein by the Lowry technique. Lowry, et al, *J. Biol. Chem.*, 93, 265, (1951). The polysaccharide showed a single line of precipitation when tested in a gel double diffusion test against rabbit antiserum specific for yeast-phase *C. albicans*.

Five different fractions were obtained:
1. Cytoplasmic cell extract;
2. Ribosomes;
3. Cell wall;
4. Cell membrane; and
5. Polysaccharide.

Fractions 2-5 (ribosome, cell wall, cell membrane and polysaccharides) have been found to have immuneaugmentative effect while fraction 1 or cytoplasmic extracts have immunesuppressive effect. Therefore, fractions 2-5 are useful as BRMs according to the invention.

b) The PER of *Corynebacterium Parvum* (CP) purchased from RIBI Immunochem. Research was used as a BRM according to the invention.

c) The MER of BCG purchased from RIBI Immunochem. Research was used as a BRM according to the invention.

d) Thymopoietin. Thymosin fraction 5 (TF5) supplied by SERVA Fine Biochemicals, Garden City Park, N.Y. was used as a BRM according to the invention with a concentration of 100 ug/ml.

e) Interleukin-1 purchased from Genzyme Co. was used as a BRM according to the invention with a concentration of 1,000 units/ml.

f) Interleukin-2 purchased from Genzyme Co. was used as a BRM according to the invention with a similar concentration of interleuken-1.

g) Lentinan purchased from ISHII Enterprises Group, Los Angeles was used as a BRM according to the invention.

h) Muramyldipeptide of BCG purchased from Syntrex Co. was used as BRM according to the invention.

EXAMPLE 2 a) June grass extract was bound to the polysacchride BRM's as follows:

1. June grass (supplied by Pharmacia Diagnostics) was dissolved in phosphate buffer saline pH 6.5 to the concentration of 2 mg/ml.

2. Different polysaccharides BRM's: Lentinan, C. Parvum (PER), Muramyldipeptide of BCG, Methanol Extract Residue (MER) of BCG, and Candida Polysaccharide from example 1 were each separately dissolved in phosphate buffer saline pH 7.2. Concentration of one mg/ml.

3. To one ml. of each polysaccharide 100/microliters of 2% periodate was added in order to convert the carbohydrate components to the free aldehyde groups.

4. This mixture of polysaccharide and periodate was stirred for ten minutes and one ml of June grass solution was added and mixed well for 3 minutes. 100 ul of sodiumborohydride was then added for stabilization of secondary amino bond and to create a covalent cross linking between the polysaccharide to the protein of the allergen.

5. The mixture was then dialysed against phosphate buffer saline for three days and after centrifugation and filtration was kept at $-20°$ C. until used.

b) June grass extract was coupled to TF5, interleukin-1 and interleukin-2 as follows:

June grass extract was coupled to TF5, interleukin-1 and interleukin-2 as follows:

June grass extract was coupled to thymopoietin TF5 Interleukin-1, interleukin-2 antigens by reacting them with EDAC (1-ethyl-3 dimethylaminopropyl) carbodimide-hydrochloride coupling agent. The reaction mechanism involves two steps: the activation of carboxyl groups, and the displacement of the nucleophile, e.g., R-NH2, releasing the EDAC as a soluble urea derivative. The activated carboxyl was coupled to the amino group in the reaction mixture. 100 ug of the TF5, 1,000 unit of the interleukin-1 and 1,000 units of interleukin-2 were separately dissolved in a carbonate buffer pH 9.6. The allergens at a concentration of about 2 mg/ml were dissolved in an acetate buffer. The pH was corrected to between 4.7 and 5. One (1) ml of protein was then added to 1 ml of allergen. The pH was then adjusted between 4.7 and 5 using HCl and 4 mg of EDAC. The reaction proceeds for 2 hours. The resulting mixture was dialysed and different fractions are separated using gel chromatography. The allergen bound to the BRM agent was then separated.

c) $\beta$-lactalbumin extract was coupled to the polysaccharide BRM's as follows:

1. $\beta$-lactalbumin (supplied by SIGMA Chemicals was dissolved in phosphate buffer saline pH 6.5 to the concentration of 2 mg/ml.

2. Different polysaccharides BRM's : Lentinan, C. Parvum (PER), Muramyldipeptide of BCG, Methanol Extract Residue (MER) of BCG, and Candida Polysaccharide from example 1 were each separately dissolved in phosphate buffer saline pH 7.2, 1 mg/ml concentration.

3. To one ml. of each polysaccharide 100/microliters of 2% periodate is added in order to convert the carbohydrate components to the free aldehyde groups.

4. This mixture of polysaccharide and periodate was stirred for ten minutes and one ul. of $\beta$-lactalbumin solution was added and mixed well for 3 minutes. 100 ul. of sodiumborohydride was then added for stabilization of secondary amino bond and to create a covalent cross linking between the polysaccharide to the protein of the allergen.

5. The mixture was then dialysed against phosphate buffer saline for three days and after centrifugation and filgration was kept at $-20°$ C. until used.

d) $\beta$-lactalbumin was coupled to TF5 interleukin-1 and interleukin-2 as follows:

$\beta$-lactalbumin extract was coupled to thymopoietin TF5 Interleukin-1, interleukin-2 antigens by reacting them with EDAC (1-ethyl-3 dimethylaminopropyl) carbodimide-hydrochloride coupling agent. The reaction mechanism involves two steps: the activation of the carboxyl groups, and the displacement of the nucleophile, e.g., R-NH2, releasing the EDAC as a soluble urea derivative. The activated carboxyl was coupled to the amino group in the reaction mixture. 100 ug of the TF5 and 1,000 unit of the interleukin-1 and 1,000 units of interleukin-2 were separately dissolved in a 1 ml of carbonate buffer pH 9.6. The allergens at a concentration of about 2 mg/ml were dissolved in 1 ml of an acetate buffer. The pH was corrected to between 4.7 and 5. One (1) ml of protein was then added to 1 ml of allergen. The pH was then adjusted between 4.7 and 5 using HCl and 4 mg of EDAC. The reaction proceeds for 2 hours. The resulting mixture was dialysed and different fractions are separated using gel chromatography. The allergen bound to the BRM is thus separated.

e) Mixture of allergen and BRM were prepared as follows:

Mixture of allergen and BRM were prepared with the exact proportion used for coupling but the crosslinking agent was excluded. For example:

1 ml of (2 mg/ml) of allergen was mixed with either 1 ml of (100 ug/ml) TF5, or separately with 1 ml of interleuken-1 and interleuken-2 1,000 units/ml. Similarly 1 ml of June Grass or $\beta$ lactalbumin (allergens) was mixed each separately with one ml of different polysaccharides BRMs: Lentinan, C. Parvum (PER), muramyldipeptide of BCG, methanol extract residue (MER) of BCG, and candida polysaccharide. The pH of all these mixtures was corrected to 7.2–7.4 and was used in the in vitro assays for measurement of histamine release and production of IgG and IgE.

EXAMPLE 3 a) Histamine Release and IgE and IgG synthesis In-Vitro

Measurement of basophil histamine release and synthesis of allergen specific IgE and IgG is presented. Briefly, human mononuclear cells from allergic and normal donors were separated, using ficoll density gradient centrifugation. After separation and counting $2 \times 10^6$ cells were initially incubated in 2 ml of basic medium (consisting of RPMI 1640 supplemented with 2 m M glutamine, 1% tryptic soy broth and 100 unit penicillin, 100 ug streptomycin, 0.25 ug fungzone/ml) or complete medium (consisting of basic medium without tryptic soy broth but supplemented with 15% heat inactivated pooled human AB serum) with or without 10, 100 and 1,000 ug/ml of allergens. At day 1, 4 and 10 samples were removed and centrifuged. Basophils were counted in the pellet and the supernatant was removed from measurements of histamine content and allergen specific IgE and IgG. Results are reported in tables 1 to 4.

b) Measurement of Histamine:

Histamine was measured, using competitive RIA technique as follows:

Histamine RIA: The histamine content of the supernatants is determined by a competitive binding radioimmunoassay with second antibody separation of antibody-ligand complexes. The assay is linear between 2 and 100 ng/ml histamine. 50 ul of supernatant is incubated at room temperature for 30 minutes with 100 ul of 3 H-histamine tracer and 100 ul anti-histamine antibody. 200 ul of precipitating second antibody is added. After 30 minutes at refrigeration temperature the duplicates tubes are centrifuged in a refrigerated centrifuge. The supernatant is aspirated and the pellet dissolved with NaOH. Scintillation cocktail is added and the radioactivity is determined in a liquid scintillation counter. Haydik I. G. Histamine Determination by Radioimmunoassay. *J. Allergy Clinical Immunology* 71:152,1983.

c) Measurement of Allergen Specific IgE and IgG:

100 ul of supernatant was transferred into U-bottom microtiter plates, coated with the allergen in duplicated, and incubated for 1 hour at room temperature. Supernatants were then decanted and wells washed 3 times with 1% BSA in Dullbecco's phosphate buffered saline. The 100 ul of alkaline phosphatase labelled anti human IgE or IgG were added to each well. After another hour of incubation at room temperature, anti IgE or anti IgG were decanted and the walls washed 3 times with 0.5% BSA in PBS. After 60 minutes, from addition of substrate P-nitrophenyl phosphate, color development measured at 405 mM. the amount of allergen specific IgE or IgG was expressed by enzyme units after comparison with IgE or IgG standard curve.

Results are summarized in Talbes 1 to 4.

TABLE 1

Binding of June Grass to different biological modifiers which increase its antigenicity but decrease its allergenicity.

| ALLERGEN BEFORE AND AFTER BINDING TO DIFFERENT BIOLOGICAL MODIFIERS | BASOPHIL HISTAMINE RELEASE IN-VITRO | IgE PRODUCTION IN-VITRO | IgG PRODUCTION IN-VITRO | IgG PRODUCTION IN-VIVO |
|---|---|---|---|---|
| JUNE GRASS (CONTROL) | +++ | +++ | − | + |
| JUNE GRASS BOUND TO (THYMOPOIETIN)(TF5) | − | − | + | ++ |
| JUNE GRASS BOUND TO INTERLEUKINS | + − | − | + | ++ |
| JUNE GRASS BOUND TO CANDIDA POLYSACCHARIDES | − | − | ++ | +++ |
| JUNE GRASS BOUND TO CORYNEBACTERIUM PARVUM | + − | + − | + | ++ |
| JUNE GRASS BOUND TO METHANOL EXTRACT OF BCG | + | + | ++ | ++ |
| JUNE GRASS BOUND TO MURAMYLDIPEPTIDE | + | + | ++ | +++ |
| JUNE GRASS & LENTINAN | − | + | ++ | ++ |

Different patients' lymphocytes with class 5 RAST according to the FADAL - NALLEBUFF scoring system to June Grass were mixed with different concentrations of June Grass or June Grass bound to the various biological response modifiers. The mixture was incubated at 37° with 5% CO₂ and 95% air for a period of 10 days. At different intervals (1, 4, 10 days) samples from culture medium were removed and examined for histamine, IgE and IgG content. The highest amount of histamine IgE and IgG was detected at days 1, 4 and 10 respectively. In addition these mixtures were injected into rabbits for measurement of IgG production in-vivo. These IgG antibodies peaked at 25–28 days post antigen injection.

TABLE 2

Mixing of June Grass to different biological modifiers which increase its antigenicity but decrease its allergenicity.

| ALLERGEN BEFORE AND AFTER MIXING TO DIFFERENT BIOLOGICAL MODIFIERS | BASOPHIL HISTAMINE RELEASE IN-VITRO | IgE PRODUCTION IN-VITRO | IgG PRODUCTION IN-VITRO | IgG PRODUCTION IN-VIVO |
|---|---|---|---|---|
| JUNE GRASS (CONTROL) | +++ | +++ | − | + |

TABLE 2-continued

Mixing of June Grass to different biological modifiers which increase its antigenicity but decrease its allergenicity.

| ALLERGEN BEFORE AND AFTER MIXING TO DIFFERENT BIOLOGICAL MODIFIERS | BASOPHIL HISTAMINE RELEASE IN-VITRO | IgE PRODUCTION IN-VITRO | IgG PRODUCTION IN-VITRO | IgG PRODUCTION IN-VIVO |
|---|---|---|---|---|
| JUNE GRASS MIXED WITH THYMOPOIETIN | + | + | + | + |
| JUNE GRASS MIXED WITH INTERLEUKINS | ++ | + | + | + |
| JUNE GRASS MIXED WITH CANDIDA POLYSACCHARIDES | + | + | ++ | ++ |
| JUNE GRASS & CORYNEBACTERIUM PARVUM | + | + | ++ | ++ |
| JUNE GRASS MIXED WITH METHANOL EXTRACT OF BCG | + | + | ++ | ++ |
| JUNE GRASS MIXED WITH MURAMYLDIPEPTIDE | ++ | + | + | ++ |
| JUNE GRASS MIXED WITH LENTINAN | + | + | ++ | ++ |

Different patients' lymphocytes with class 5 RAST according to the FADAL - NALLEBUFF scoring system to June Grass were mixed with different concentrations of June Grass or June Grass mixed with different biological response modifiers. The mixture was incubated at 37° with 5% $CO_2$ and 95% air for a period of 10 days. At different intervals (1, 4, 10 days) samples from culture medium were removed and examined for histamine, IgE and IgG content. The highest amount of histamine IgE and IgG was detected at days 1, 4, and 10 respectively. In addition these mixtures were injected into rabbits for measurement of IgG production in-vivo. These IgG antibodies peaked at 20–31 days post antigen injection.

TABLE 3

Covalent Binding of allergen ($\beta$-Lactalbumin) to different biological modifiers and decrease in its allergenicity.

| ALLERGEN BEFORE AND AFTER COVALENT BINDING TO DIFFERENT BIOLOGICAL MODIFIERS | BASOPHIL HISTAMINE IN-VITRO | IgE PRODUCTION IN-VITRO | IgG PRODUCTION IN-VITRO | IgG PRODUCTION IN-VIVO |
|---|---|---|---|---|
| $\beta$-LACTALBUMIN (FROM MILK) (CONTROL) | ++ | ++ | + | ++ |
| $\beta$-LACTALBUMIN BOUND TO THYMOPOIETIN | − | − | ++ | ++ |
| $\beta$-LACTALBUMIN BOUND TO INTERLEUKINS | − | + | ++ | ++ |
| $\beta$-LACTALBUMIN BOUND TO CANDIDA POLYSACCHARIDES | − | − | + | + |
| $\beta$-LACTALBUMIN BOUND TO CORYNEBACTERIUM PARVUM | − | − | ++ | ++ |
| $\beta$-LACTALBUMIN BOUND TO METHANOL EXTRACT OF BCG | − | − | ++ | ++ |
| $\beta$-LACTALBUMIN BOUND TO MURAMYLDIPEPTIDE | + | + | ++ | +++ |
| $\beta$-LACTALBUMIN & LENTINAN | − | + | +++ | +++ |

Different patients' lymphocytes with class 4 RAST according to FADAL - NALLEBUFF scoring system to $\beta$-lactalbumin, were mixed with different concentrations of $\beta$-lactalbumin or $\beta$-lactalbumin bound to various biological response modifiers or lymphokine inducers. The mixture was incubated at 37° degrees with 5% $CO_2$ and 95% air for a period of 10 days. At different intervals (1, 4, 10 days) samples from culture medium were removed and examined for histamine, IgE and IgG content. The highest amount of histamine IgE and IgG was detected at days 1, 4, and 10 respectively. In addition these mixtures were injected into rabbits for measurement of IgG production in-vivo. These IgG antibodies peaked at 21–27 days post antigen injection.

TABLE 4

Mixing of allergen ($\beta$-Lactalbumin) with different biological modifiers and decrease in its allergenicity.

| ALLERGEN BEFORE AND AFTER MIXING WITH DIFFERENT BIOLOGICAL MODIFIERS | BASOPHIL HISTAMINE IN-VITRO | IgE PRODUCTION IN-VITRO | IgG PRODUCTION IN-VITRO | IgG PRODUCTION IN-VIVO |
|---|---|---|---|---|
| $\beta$-LACTALBUMIN (CONTROL) | +++ | +++ | + | ++ |
| $\beta$-LACTALBUMIN MIXED WITH THYMOPOIETIN | + | + | ++ | ++ |
| $\beta$-LACTALBUMIN MIXED WITH INTERLEUKINS | + | + | ++ | +++ |
| $\beta$-LACTALBUMIN MIXED WITH CANDIDA POLYSACCHARIDES | + | + | ++ | ++ |
| $\beta$-LACTALBUMIN MIXED WITH CORYNBACTERIUM PARVUM | + | − | ++ | ++ |
| $\beta$-LACTALBUMIN MIXED WITH METHANOL EXTRACT OF BCG | + | + | ++ | ++ |
| $\beta$-LACTALBUMIN MIXED WITH MURAMYLDIPEPTIDE | + | + | ++ | ++ |
| $\beta$-LACTALBUMIN MIXED WITH LENTINAN | + | + | ++ | ++ |

Different patients' lymphocytes with class 4 RAST according to the FADAL - NALLEBUFF scoring system to $\beta$-lactalbumin, were mixed with different concentrations of $\beta$-lactalbumin or $\beta$-lactalbumin mixed with different biological response modifiers. The mixture was incubated at 37° degrees with 5% $CO_2$ and 95% air for a period of 10 days. At different intervals (1, 4, 10 days) samples from culture medium were removed and examined for histamine, IgE and IgG was detected at days 1, 4, and 10 respectively. In addition these mixtures were injected into rabbits for measurement of IgG production in-vivo. These IgG antibodies were peaked at 21–27 days post antigen injection.

Table 1 compares the effect of the covalently bound June grass allergen—BRM with a control June grass extract allergen alone.

Table 2 compares the effect of a mixture of BRM and June grass extract with a control June grass extract alone.

Table 3 compares the effect of the covalently bound β-Lactalbumin allergen—BRM with a control β-Lactalbumin extract allergen alone.

Table 4 compares the effect of a mixture of BRM and β-Lactalbumin extract with a control β-Lactalbumin extract alone.

Figure 2:
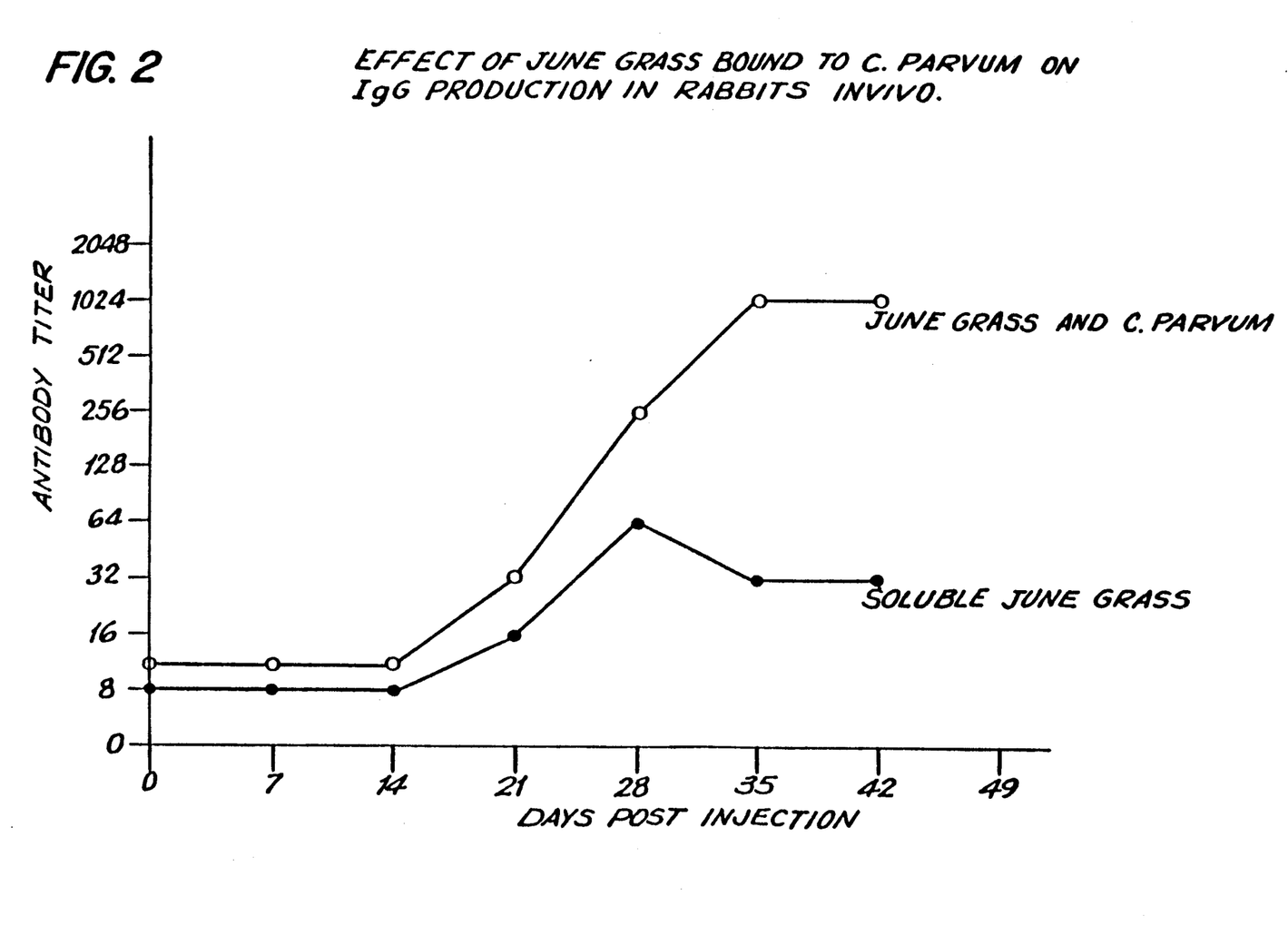
FIG. 2 is a graphical comparison of the effects of the claimed invention on allergen specific IgG production in vivo.

In another aspect of the invention as demonstrated by FIG. 2, according to the invention the production of allergen specific IgG is enhanced in vivo when an allergen—BRM combination is administered. FIG. 2 graphically reports the effects of June grass and June grass bound to *C. Parvum* on IgG production in rabbits. Different rabbits were injected with 2 mg of soluble June grass antigens or with June grass bound to *C. Parvum*. Different days post injection serum was prepared and was measured by Elisa for the specific levels of IgG against soluble June grass as shown in FIG. 2. The results clearly showed significant enhancement of IgG anti June grass antigen binding to *C. Parvum*.

It should be understood by those skilled in the art that various modifications may be made in the present invention but not departing from the spirit and scope thereof as described in the specification and defined in the appending claims. While the invention has been described by reference to specific embodiments, this was for the purpose of illustration only and should not be construed to limit the spirit or scope of the invention.

I claim:

1. A protein conjugate useful in allergy immunotherapy comprising an allergen which causes IgE mediated allergic response conjugated to a biological response modifier (BRM) selected from the group of thymic hormones.

2. The protein conjugate according to claim 1 wherein the BRM is thymic hormone factor TF5.

3. The protein conjugate of claim 1 wherein the allergen is selected from the group of pollen and β-lactalbumin.

4. The protein conjugate of claim 1 wherein the allergen is grass pollen.

5. The protein conjugate of claim 1 where the allergen is β-lactalbumin.

6. The protein conjugate of claim 1 where the allergen is June grass.

7. A method of preparing an immunotherapy injectant comprising conjugating a BRM selected from the group of thymic hormones with an allergen extract which causes IgE mediated allergic response and which is used in allergy immunotherapy.

8. A method of immunotherapy comprising periodically injecting an allergic person with a therapeutically effective amount of the protein conjugate containing an allergen to which the person demonstrates an allergic reaction of claim 1 mixed with a pharmaceutically acceptable carrier.

9. A method of immunotherapy comprising periodically injecting an allergic person with a protein conjugate of an allergen and thymic hormone factor TF5 and a pharmaceutically acceptable carrier.

10. A method of enhancing production of allergen specific IgG in mammals comprising injecting in the mammal a therapeutically effective amount of thymic hormones coupled to an allergen to which said mammal exhibits an IgE mediated allergic reaction.

* * * * *